(12) United States Patent
Noar

(10) Patent No.: US 11,369,310 B2
(45) Date of Patent: Jun. 28, 2022

(54) METHOD AND SYSTEM FOR PREDICTING SUCCESSFUL TREATMENT METHODS AND OUTCOMES OF BODILY TISSUE DISORDERS BASED ON ENERGY ACTIVITY OF THE TISSUE

(71) Applicant: Mark D. Noar, Owings Mills, MD (US)

(72) Inventor: Mark D. Noar, Owings Mills, MD (US)

( * ) Notice: Subject to any disclaimer, the term of this patent is extended or adjusted under 35 U.S.C. 154(b) by 478 days.

(21) Appl. No.: 15/598,131

(22) Filed: May 17, 2017

(65) Prior Publication Data
US 2017/0332961 A1   Nov. 23, 2017

Related U.S. Application Data

(60) Provisional application No. 62/338,050, filed on May 18, 2016.

(51) Int. Cl.
*A61B 5/00* (2006.01)
*G16H 50/70* (2018.01)
(Continued)

(52) U.S. Cl.
CPC .......... *A61B 5/4839* (2013.01); *A61B 5/0059* (2013.01); *A61B 5/296* (2021.01); *A61B 5/392* (2021.01); *A61B 5/4238* (2013.01); *A61B 5/4836* (2013.01); *A61B 5/4848* (2013.01); *A61B 5/7225* (2013.01); *A61B 5/7275* (2013.01); *A61F 7/00* (2013.01); *A61H 23/00* (2013.01); *A61M 29/00* (2013.01); *A61N 2/00* (2013.01); *A61N 5/06* (2013.01);
(Continued)

(58) Field of Classification Search
None
See application file for complete search history.

(56) References Cited

U.S. PATENT DOCUMENTS 5,292,344 A * 3/1994 Douglas ................... A61B 5/03
607/40
6,351,665 B1 * 2/2002 Koch ................ A61B 5/04884
600/546

(Continued)

OTHER PUBLICATIONS

Chang, Full-Young, et al. "Electrogastrographic characteristics in patients of stomach cancer." Digestive diseases and sciences 46.7 (2001): 1458-1465. (Year: 2001).*

(Continued)

*Primary Examiner* — Jacqueline Cheng
*Assistant Examiner* — Jairo H Portillo
(74) *Attorney, Agent, or Firm* — Manelli Seller PLLC; Edward Stemberger

(57) ABSTRACT

A method of predicting successful treatment of disorders of bodily tissue includes obtaining, with a device, energy signal data from the bodily tissue of a patient. The obtained energy signal data is analyzed in a controller to determine an activity score value associated with the bodily tissue. The activity score value is compared, in the controller, to a threshold value, with the threshold value being based on energy signal data from the same bodily tissue of normal, disease free patients. Based on the comparison, a probability of success of a particular therapy in treating the bodily tissue is determined. A system for performing the method is also disclosed.

6 Claims, 4 Drawing Sheets

Graph 1

(51) Int. Cl.
*G16H 50/20* (2018.01)
*G16H 50/30* (2018.01)
*A61B 5/296* (2021.01)
*A61B 5/392* (2021.01)
*A61F 7/00* (2006.01)
*A61H 23/00* (2006.01)
*A61M 29/00* (2006.01)
*A61N 2/00* (2006.01)
*A61N 5/06* (2006.01)
*A61N 5/10* (2006.01)
*A61B 5/08* (2006.01)

(52) U.S. Cl.
CPC ............... *A61N 5/10* (2013.01); *G16H 50/20* (2018.01); *G16H 50/30* (2018.01); *G16H 50/70* (2018.01); *A61B 5/08* (2013.01); *A61H 2201/0153* (2013.01); *A61H 2201/10* (2013.01); *A61H 2230/405* (2013.01); *A61H 2230/605* (2013.01)

(56) References Cited

U.S. PATENT DOCUMENTS

| | | |
|---|---|---|
| 7,160,254 B2 | 1/2007 | Noar |
| 8,417,342 B1 | 4/2013 | Abell |
| 8,880,174 B1 | 11/2014 | Abell et al. |
| 2004/0068207 A1* | 4/2004 | Tabata ............... A61P 35/00 601/2 |
| 2004/0243211 A1* | 12/2004 | Colliou ............. A61N 1/36007 607/133 |
| 2005/0149142 A1* | 7/2005 | Starkebaum ....... A61N 1/36007 607/40 |
| 2006/0282019 A1* | 12/2006 | Hamilton ............... A61B 17/42 600/591 |
| 2007/0060785 A1* | 3/2007 | Freeman ............... A61H 31/007 600/16 |
| 2008/0118918 A1 | 5/2008 | Licinio et al. |
| 2009/0177123 A1* | 7/2009 | Peterson ........... A61M 37/0092 601/2 |
| 2010/0049274 A1 | 2/2010 | Cholette |
| 2011/0137105 A1* | 6/2011 | Liang ...................... H03K 3/78 600/13 |
| 2011/0295335 A1* | 12/2011 | Sharma ............. A61N 1/36007 607/40 |
| 2012/0065494 A1* | 3/2012 | Gertner .................. A61B 8/06 601/2 |
| 2013/0041683 A1 | 2/2013 | Boissel |
| 2013/0046150 A1* | 2/2013 | Devanaboyina ..... A61B 5/6823 600/382 |
| 2014/0058282 A1* | 2/2014 | O'Grady ............ A61B 5/04884 600/546 |
| 2014/0088462 A1* | 3/2014 | Mishelevich .......... A61B 5/392 601/2 |
| 2014/0275748 A1* | 9/2014 | Dunki-Jacobs ...... A61B 5/4839 600/37 |
| 2016/0113559 A1* | 4/2016 | Lynch .................... A61B 5/746 600/301 |
| 2018/0001184 A1* | 1/2018 | Tran ....................... G06F 1/163 |

OTHER PUBLICATIONS

International Search Report & Written Opinion in PCT/US2017/033173 dated Aug. 14, 2017.
European Search Report and Opinion in EP 17800117.8 dated Sep. 18, 2019

* cited by examiner

TABLE 1. Associations of Post-Dilation Success (%-Emptying>60% at 120 Mins) with Predilation 3CPM Activity and Model Fit (logistic regression model results)

| Odds Ratio (OR) (95%CI) p-value | Individual Predictors | | | | | Joint Model (all four 3CPM measures) |
|---|---|---|---|---|---|---|
| 3CPM: Baseline | OR=1.06 (1.00,1.13) p=0.057 | | | | | 1.14 0.96,1.35 0.15 |
| 3CPM: 10 mins | | 1.13 0.98,1.30 0.088 | | | | 1.23 0.92,1.65 0.157 |
| 3CPM: 20 mins | | | 1.04 0.98,1.11 0.146 | | | 1.08 0.94,1.23 0.275 |
| 3CPM: 30 mins | | | | 1.02 0.97,1.07 0.397 | | 0.93 0.82,1.05 0.246 |
| Mean 3cpm (0-30mins) | | | | | 3.8 1.03,13.99 0.044 | |
| Model Fit | (lower AIC is better) | | | | | |
| AIC | 23.17 | 20.49 | 25.06 | 26.84 | 22.3 | 20.79 |
| Discrimination | (higher AUC is better) | | | | | |
| AUC | 0.81 | 0.85 | 0.71 | 0.62 | 0.8 | 0.95 |
| Calibration | (lower Chi-Sq \ higher p-values are better) | | | | | |
| HL Chi-Sq | 4.39 | 11.28 | 7.12 | 11.5 | 7.07 | 0.73 |
| HL pval | 0.82 | 0.19 | 0.52 | 0.18 | 0.53 | 1.00 |

FIG. 4

| TABLE 2. Classification with a threshold cutoff of Pr(S) >= 0.59 (Activity Threshold) | | | | | | |
|---|---|---|---|---|---|---|
| | ------- True ------- | | | Sensitivity | Pr(+D) | 96.15% |
| | | No | | Specificity | Pr(-~D) | 75.00% |
| Classified | Success | Success | Total | | | |
| + | 25 | 1 | 26 | Positive predictive value | Pr(D+) | 96.15% |
| - | 1 | 3 | 4 | Negative predictive value | Pr(~D-) | 75.00% |
| Total | 26 | 4 | 30 | | | |
| | | | | False + rate for true ~D | Pr(+~D) | 25.00% |
| | | | | False - rate for true D | Pr(-D) | 3.85% |
| | | | | False + rate for classified + | Pr(~D+) | 3.85% |
| | | | | False - rate for classified - | Pr(D-) | 25.00% |
| | | | | Correctly classified | | 93.33% |

FIG. 5

Graph 1

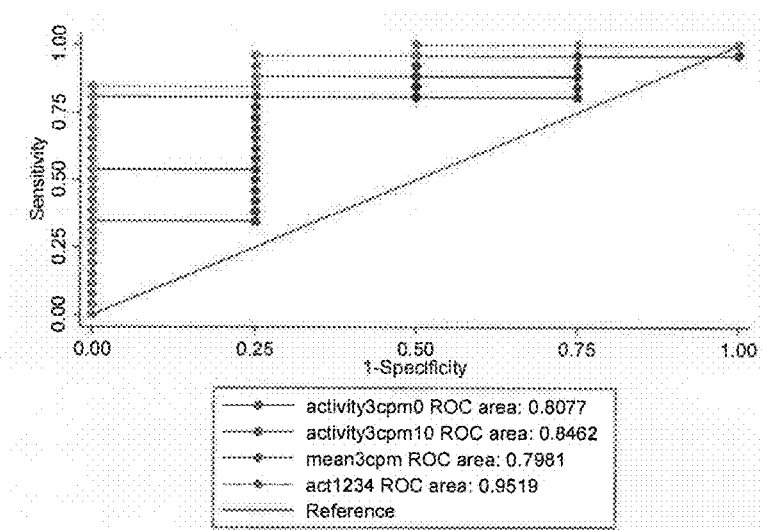

FIG. 6

METHOD AND SYSTEM FOR PREDICTING SUCCESSFUL TREATMENT METHODS AND OUTCOMES OF BODILY TISSUE DISORDERS BASED ON ENERGY ACTIVITY OF THE TISSUE

This application claims priority from U.S. Provisional Application No. 62/338,050, filed on May 18, 2016, the content of which is hereby incorporated by reference in its entirety herein.

BACKGROUND

U.S. Pat. No. 7,160,254, hereby incorporated by reference in its entirety herein, discloses an Electrogastrogram (EGG) system and method to gather and evaluate myoelectric signals from intra-abdominal organs and other motility based organs. The EGG system aids in the diagnosis of organ disorders upon analyzing the EGG data. Although the EGG system is well suited for its intended purpose, there is a need to be able to predict, with high accuracy, organ disorders based on electrical signal data obtained from the organ.

SUMMARY

An objective of the embodiment is to fulfill the need referred to above. In accordance with the principles of the embodiment, this objective is achieved by providing a method of predicting successful treatment of disorders of bodily tissue includes obtaining, with a device, energy signal data from the bodily tissue of a patient. The obtained energy signal data is analyzed in a controller to determine an activity score value associated with the bodily tissue. The activity score value is compared, in the controller, to a threshold value, with the threshold value being based on energy signal data from the same bodily tissue of normal, disease free patients. Based on the comparison, a probability of success of a particular therapy in treating the bodily tissue is determined.

In accordance with another aspect of an embodiment, a method predicts successful treatment of disorders of bodily organs by performing an electrogastrogram on a bodily organ of a patient. An activity score value associated with the bodily organ based on data from the electrogastrogram is determined in a controller. The controller compares the activity score value to a threshold value, with the threshold value being based on electrogastrogram data from the same bodily organ of normal, disease free patients. Based on the comparison, a probability of success of a particular therapy in treating the bodily organ is determined.

In accordance with yet another aspect of an embodiment, a system for predicting successful treatment of disorders of bodily tissue includes at least one sensor constructed and arranged to obtain energy signal data from the bodily tissue of a patient. A controller, having a processor circuit, is constructed and arranged to 1) determine an activity score value associated with the bodily tissue based on data from the at least one sensor, and 2) compare the activity score value to a threshold value, with the threshold value being based on energy signal data from the same bodily tissue of normal, disease free patients to determine, based on the comparison, a probability of success of a particular therapy for treating the bodily tissue. The system can also include therapy delivery structure constructed and arranged to deliver the particular therapy to the bodily tissue.

Other objectives, features and characteristics of the present embodiment, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which:

FIG. 4 shows TABLE 1, "Associations of Post-Dilation Success (%-Emptying>60% at 120 Mins) with Predilation 3 CPM Activity and Model Fit (logistic regression model results)".

FIG. 5 shows TABLE 2, "Classification with a threshold cutoff of Pr(S)>=0.59 (Activity Threshold)".

FIG. 6 shows Graph 1, "Linear regression analysis of the association of Post-Dilation Success".

DETAILED DESCRIPTION OF EXAMPLE EMBODIMENTS

Figure 1:
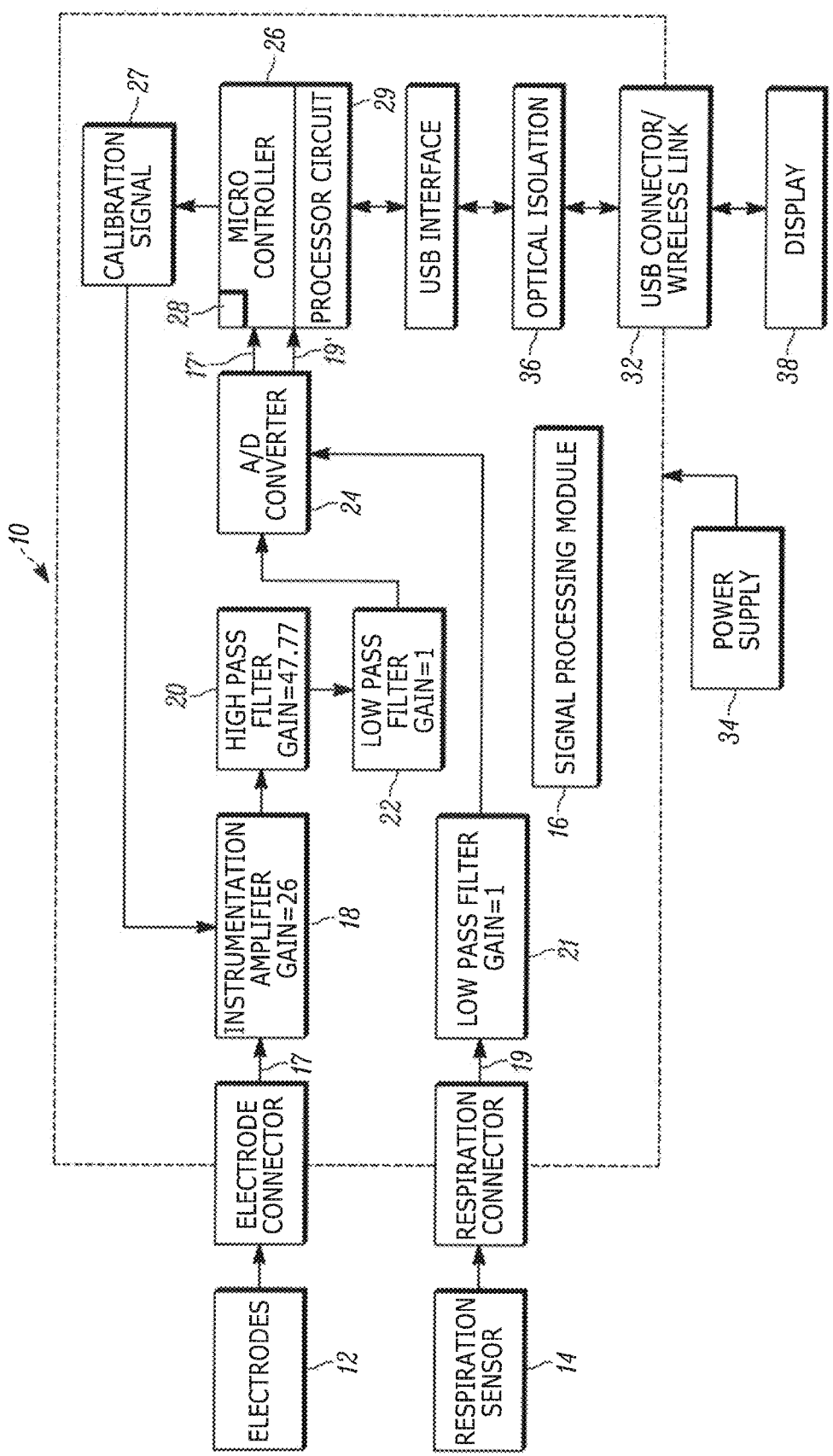
FIG. 1 a block diagram of an EGG system provided in accordance with an embodiment.

It is known from U.S. Pat. No. 7,160,254 that EGG and water load test accurately detects functional gastric outlet obstruction with associated gastroparesis. In addition, balloon dilation of the pylorus, in addition to other pyloric therapies, has been shown to correct gastroparesis. With reference to TABLES 1, 2 and Graph 1, as shown in FIGS. 4-6, respectively, and, in accordance with the embodiment, EGG data and data from balloon dilation of the pylorus can be used to predict when balloon dilation should be used to correct gastroparesis.

With reference to TABLE 2 in FIG. 5, a Activity Threshold is established based upon 3 CPM (cycles per minute) frequency data from the stomach of normal, disease free patients. In the example, if the Activity Score> or =0.59 (Activity Threshold), there is a 96.15% chance of successful treatment of gastroparesis by balloon dilation of the patient's pylorus (See TABLE 2). If the Activity Score obtained in below the Activity Threshold of 0.59, balloon dilation of the pylorus should not be performed since, based on this predictive model, it will not help the patient.

The linear regression analysis in Graph 1 of FIG. 6 demonstrates the derivation of gastricmyoelectrical motor activity (GMA) 3 cpm threshold (GMAT) predicted gastric emptying normalization and symptomatic improvement after pyloric balloon dilation. GMAT sensitivity and specificity predicting normalization were 96.15% and 75.00% respectively with 93.33% of patients correctly classified. Graph 1 shows Linear regression analysis of the association of Post-Dilation Success (% Emptying >60% at 120 minutes) with Pre-Dilation 3 cpm Activity and Model Fit, Joint Activity Score Linear Regression: −8.299+0.128(3 cpm0 min)+0.210*(3 CPM10 min)+0.074*(3 cpm20 min)−0.073*(3 cpm30 min), Threshold value >0.59

The Activity Score and baseline Activity Threshold calculation will serve as the starting point for looking at potentially all possible treatments of all disorders affecting stomach emptying and/or function.

Based on EGG data obtained and the post-dilation success, a formula has been determined using statistical analysis and linear regression to predict the success of the balloon dilation treatment of the pylorus.

The formula is as follows:

$$\text{Activity Score} = -8.299 + 0.128*(3\ \text{CPM0 min}) + 0.210*(3\ \text{CPM10 min}) + 0.074*(3\ \text{CPM20 min}) - 0.073*(3\ \text{CPM30 min}),$$

where 3 CPM is a measure of a level of 3 CPM frequency activity of the bodily organ at the indicated time period in minutes.

An example of the method steps for predicting success of treatment of bodily organs are:
1. Perform EGG of any type or more specifically with water load to obtain gastric motility data from a bodily organ.
2. Data is analyzed for levels of 3 CPM activity as well as tachygastria and bradygastria.
3. The data is collected and incorporated and analyzed using the developed formula to provide a resultant Activity Score.
4. The Activity Score is scaled against an established Activity Threshold based upon EGG data from the bodily organ of normal, disease free patients.
5. If the level of the Activity Score is above a treatment and disease specific determined threshold (Activity Threshold), therapy is reported as having a high or low probability of success.
6. Operator selects disease or state of gastric disorder and type of intended therapy.
7. Operator activates calculation key/icon.
8. Device provides information regarding the treatment and likelihood of success for the given disorder.

An example of the EGG System for obtaining and processing the EGG data of the method can be of the type disclosed U.S. Pat. No. 7,160,254. Thus, as shown in FIG. 1, the system 10 includes electrodes 12 (preferably two or three) and a respiratory sensor 14 connected to a single Signal Processing Module 16 (SPM). A standard instrumentation amplifier 18 provides the first gain stage for the electrode(s) signal 17. A high pass filter 20 provides additional gain and is followed by a low pass filter 22. The respiration signal 19 is filtered by low pass filter 21 and is then passed on to a 16-bit A/D converter 24. The electrode signal 17 is also passed to the on board 16-bit A/D converter 24. A digitized electrode signal 17' and a digitized respiration signal 19' are each passed to a micro-controller 26, which coordinates data transfer to a host computer 28 and printer 30 via a standard Universal Serial Bus (USB) connection, or a wireless signal transmitter 32. The A/D converter 24 can be part of the microcontroller 26. In this embodiment, the micro-controller 26 includes a processor circuit 27 that determines the Activity Score via the formula noted above. Thus, the micro-controller or control device 26 can be considered a processing device. Micro-controller 28 also includes storage 28 that provides enough on-board memory to store an entire exam's worth of data for later download. Optical isolation 36 is necessary for any hardwired (e.g., cable connected) communication system for patient electrical isolation; the wireless system enhances patient isolation but at considerable additional cost and complexity. Power is provided by power supply 34. A display 38 displays data to an operator.

Examples of use of the system and method described herein include, but are not limited to:

Example A

1. Perform EGG study
2. Obtain EGG data and analyze data using standardized methodology
3. Select disease state: Gastroparesis
4. Select intended treatment method: Balloon Dilation Pylorus
5. Activate calculation key/icon
6. Numeric value of Activity Score at or above Activity Threshold for Successful Dilation of Pylorus, then:
   a. Perform dilation
7. Numerical value of Activity Score below Activity Threshold for Successful Dilation of Pylorus, then:
   a. Do not perform dilation, investigate other modalities
      i. BOTOX injection, pacemaker, etc.

Example B

1. Perform EGG study
2. Obtain EGG data and analyze data using standardized methodology
3. Select disease state: Gastroparesis
4. Select intended treatment method: Pacemaker
5. Activate calculation key/icon
6. Numeric value of Activity Score above Activity Threshold for pacemaker insertion success, then:
   a. Place pacemaker
7. Numerical value of Activity Score below Activity Threshold for pacemaker insertion success, then:
   a. Do not place pacemaker, investigate other modalities
      i. BOTOX injection, dilation, medication, etc.

Example C

1. Perform EGG study
2. Obtain EGG data and analyze data using standardized methodology
3. Select disease state: Bradygastria, good 3 CPM signal
4. Select intended treatment method: Metoclopramide medication
5. Activate calculation key/icon
6. Numeric value of Activity Score at or above Activity Threshold for Metoclopramide success, then:
   a. Put patient on medication
7. Numerical value of Activity Score below Activity Threshold for Metoclopramide success, then:
   b. Do not give Metoclopramide, investigate other modalities
      i. Alternative medication, etc.

Although the embodiments and examples above have been described using the conventional EGG system to obtain electrical activity data from an organ, any method or system of obtaining electrical data from any bodily tissue can be employed to obtain the data.

Figure 2:
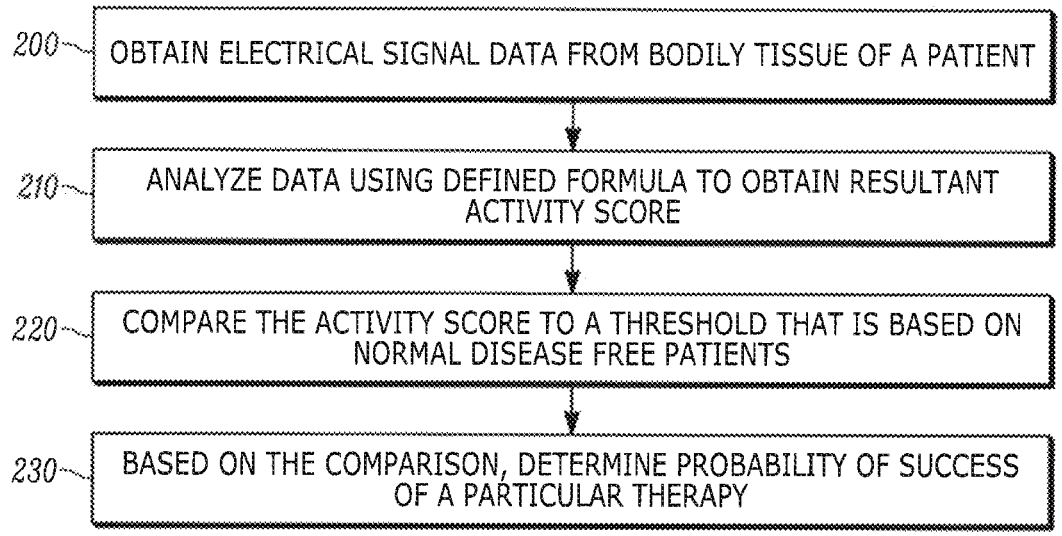
FIG. 2. is a flowchart of method steps of an embodiment.

An example of an algorithm for performing steps of an embodiment of the invention is shown in FIG. 2. In step 200, electrical signal data is obtained from bodily tissue of a patient. An EGG system or any other electrical signal obtaining system can be employed. In step 210, the data obtained is analyzed preferably using the above defined formula, or other similarly obtained formula specific to data of the bodily tissue, to obtain a resultant activity score (e.g., Activity Score as noted above). In step 220, the Activity Score is compared to a threshold (e.g., the Activity Threshold as noted above). The threshold is based on electrical activity data from the same bodily tissue of normal, disease free patients. In step 230, based on the comparison, a probability of success of a particular therapy is determined. The therapy can by any known therapy such as drug delivery, surgery, dilation, energy treatment, etc. For example, if the Activity Score is above the Activity Threshold, success of the therapy is likely and thus is performed. However, if the Activity Score is below the Activity Threshold, success of the therapy is unlikely and thus, should not be performed.

As used herein, "bodily tissue" can include bodily organs or tissue that comprises non-organ parts of the body. For example, besides organs, the tissue can be bones, muscles, and nerves. Tissue can include joints and articulations that are combinations of tissues.

Every tissue has its own specific electrical signal or generated electromagnetic field, which likely conveys health and disease information. Distinguishing healthy signals from disease signals or fields via calculations allows identification of healing point goals. Therapy, such as energy, returned to "tune" the field back to normal can then be applied to effect healing. As used herein, energy is a very broad term and can be used to mean electrical, magnetic, radiation, heat, light, vibration or other yet unknown forms of energy. Transmission of the energy can include: direct contact, and/or transmission via or through a medium such as air, water, etc.

Figure 3:
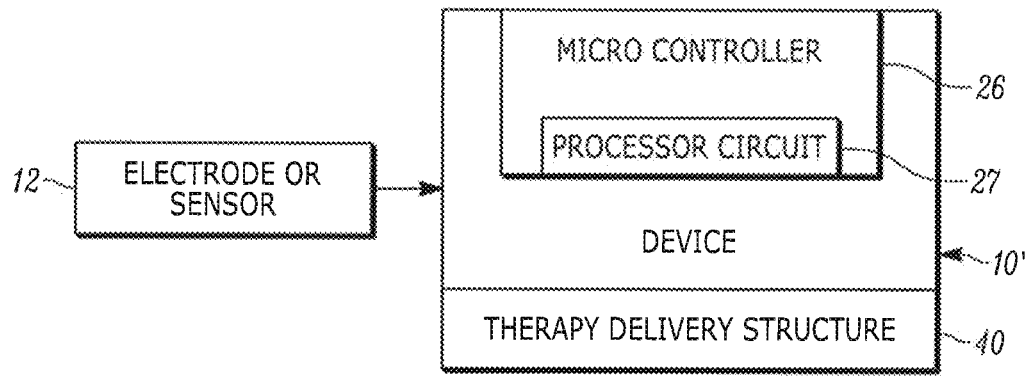
FIG. 3 is a block diagram of a device for predicting successful treatment of disorders of bodily tissue and for delivering therapy to the bodily tissue in accordance with and embodiment.

With reference to FIG. 3, the above steps can be implemented by using a physical, handheld device 10' that, as an example, can include all elements of the device 10 of FIG. 1. Thus, device 10' includes the micro-controller 26 and processing circuit 27, but can also include therapy delivery structure 40 configured to deliver the therapy, as noted above, to the defective organ. The device 10' is also configured to obtain energy signal data from the electrodes or sensors 12. As also noted above, the device 10' and method is not limited motility based organs and can be employed with any bodily tissue from which energy data signals can be obtained.

There are conventional devices that influence tissues by delivery of energy. These devices usually deliver metered amounts of energy over specific time based upon clinical studies demonstrating effect. For example, a bionicaire knee device delivers electric 7.5 CPM energy via direct contact which will regrow knee cartilage. A Stretta device delivers radio-frequency energy which generates heat in tissue and causes esophageal muscle to grow. A similar device in the bronchi delivers 65 degree centigrade heat to change bronchial smooth muscle.

The device 10' of the embodiment is different from these conventional devices since it measures the health or disease of the tissue/organ, then delivers metered and monitored therapy (e.g., such as energy noted above) with expected success rates based upon algorithmic calculations for desired effect. For example, 3 CPM EGG signals directly correlate with integrity of the ICC (interface cells required for healthy function of contraction). Level of 3 CPM calculates success of electrical stimulation in correcting gastroparesis using a stimulator.

The device 10' and method disclosed herein, at a more basic level, distinguishes disease states based upon obtaining energy (e.g., electrical, magnetic, radiant or other types of energy) signal data from abnormal tissue, compares the obtained data against normal tissue data, and calculates rates of successful treatment of the abnormal tissue and if therapy is calculated to be successful, delivers energy to the tissue to return of the tissue to normal energy levels associated with health. For example, after certain amount of time using stimulation of abnormal tissue, a healthy signal returns to the tissue and stimulation is no longer needed. In the example disclosed above, pyloric dilation corrects obstruction and allows tissue energy levels to return to normal. Obtaining of the energy signal data from the tissue and the administration of the therapy need not to be from a direct connection with the tissue. Air transmission at a distance from the tissue and other transmission methods are contemplated.

The device 10' senses or obtains energy of tissues and determines abnormal tissue or tissue that is out of place. The device 10' can include an EGG system that can detect alternate energy levels consistent with other diseases such as endometriosis in the abdomen, tumors, etc.

The operations and algorithms described herein can be implemented as executable code within the micro-controller or control device 26 having processor circuit 27 as described, or stored on a standalone computer or machine readable non-transitory tangible storage medium that are completed based on execution of the code by a processor circuit implemented using one or more integrated circuits. Example implementations of the disclosed circuits include hardware logic that is implemented in a logic array such as a programmable logic array (PLA), a field programmable gate array (FPGA), or by mask programming of integrated circuits such as an application-specific integrated circuit (ASIC). Any of these circuits also can be implemented using a software-based executable resource that is executed by a corresponding internal processor circuit such as a microprocessor circuit (not shown) and implemented using one or more integrated circuits, where execution of executable code stored in an internal memory circuit causes the integrated circuit(s) implementing the processor circuit to store application state variables in processor memory, creating an executable application resource (e.g., an application instance) that performs the operations of the circuit as described herein. Hence, use of the term "circuit" in this specification refers to both a hardware-based circuit implemented using one or more integrated circuits and that includes logic for performing the described operations, or a software-based circuit that includes a processor circuit (implemented using one or more integrated circuits), the processor circuit including a reserved portion of processor memory for storage of application state data and application variables that are modified by execution of the executable code by a processor circuit. The memory circuit 28 can be implemented, for example, using a non-volatile memory such as a programmable read only memory (PROM) or an EPROM, and/or a volatile memory such as a DRAM, etc.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:
1. A method of predicting successful treatment of disorders of motility based bodily organs, the method comprising the steps of:
performing an electrogastrogram on a bodily organ of a patient;

determining, in a controller, an activity score value associated with the bodily organ based on data from the electrogastrogram;

comparing, in the controller, the activity score value to a specific disease and specific treatment threshold value, with the specific disease and specific treatment threshold value being based on energy signal data including a specific electrical signal or electromagnetic field from the same bodily tissue of normal, disease free patients; and based on the comparison, predicting, in the controller, a probability of success of the specific treatment for the specific disease prior to treating the bodily tissue, wherein, if the comparison indicates a likelihood of success of the specific treatment, the method further includes:

delivering the specific treatment to the organ, wherein bodily organ is a stomach and the step of determining the activity score value includes using the formula:

$$\text{activity score value} = -8.299 + 0.128*(3\ \text{CPM0 min}) + 0.210*(3\ \text{CPM10 min}) + 0.074*(3\ \text{CPM20 min}) - 0.073*(3\ \text{CPM30 min}),$$

where 3 CPM is a measure of cycles per minute of activity of the stomach at certain time periods, in minutes.

2. The method of claim 1, wherein the step of delivering the specific treatment includes at least one of:

dilating tissue of the patient, performing surgery on the patient, delivering a drug to the patient, or delivering energy to the organ, as the specific treatment to restore normal energy patterns to the bodily organ.

3. The method of claim 1, wherein the analyzing step incudes using a processor circuit in the controller to execute the formula to determine the activity score value.

4. The method of claim 1, wherein the step of performing the electrogastrogram includes using an electrogastrogram system.

5. The method of claim 1, wherein the step of delivering the specific treatment includes delivering energy to the bodily organ wherein the energy includes at least one of electrical, magnetic, radiation, heat, light, or vibration energy.

6. The method of claim 5, wherein the step of delivering energy includes using a therapy delivery structure to deliver the energy.

* * * * *